United States Patent [19]

Borresen

[11] Patent Number: 5,190,856
[45] Date of Patent: Mar. 2, 1993

[54] METHOD AND APPARATUS FOR DETECTING SINGLE BASE MUTATIONS IN DNA WITH DENATURING GRADIENT ELECTROPHORESIS

[76] Inventor: Anne-Lise Borresen, Tollef Gravs v. 38, N-1342 Jar, Norway

[21] Appl. No.: 381,405

[22] PCT Filed: Oct. 3, 1988

[86] PCT No.: PCT/NO88/00074
§ 371 Date: May 31, 1989
§ 102(e) Date: May 31, 1989

[87] PCT Pub. No.: WO89/02930
PCT Pub. Date: Apr. 6, 1989

[30] Foreign Application Priority Data

Oct. 2, 1987 [NO] Norway ................. 874164

[51] Int. Cl.⁵ ............................. C12Q 1/68
[52] U.S. Cl. ............................. 435/6; 435/40; 435/173; 435/289; 435/290; 435/291; 435/300; 435/310; 435/803; 435/973; 436/501; 436/809; 935/19; 935/78; 935/86
[58] Field of Search .............. 435/6, 291, 300, 310, 435/40, 173, 289, 290, 803, 973; 436/501, 809; 935/19, 78, 86

[56] References Cited

U.S. PATENT DOCUMENTS

4,292,161  9/1981  Hoefer et al. ................. 204/299 R

OTHER PUBLICATIONS

Bethesda Research Labs Catalog (1985) p. 80.
Reiser et al., (1978) Biochem. and Biophys. Res. Comm., vol. 85, No. 3, pp. 1104–1112.
Myers et al., (1985) Nuc. Acids Res., vol. 13, No. 9, pp. 3131–3145.
Fischer, S. G. and Lerman, L. S., Proc. Natl. Acad. Sci., USA, vol. 80 pp. 1579–1583, Mar. 1983.
Borresen, A. L. (1986), Annals of Clinic. Res., vol. 18, pp. 258–263.
R. M. Myers, et al., (Molecular Biology of Homo Sapiens, Cold Spring Harbor Lab., 1986, pp. 275–284).
L. S. Lerman, et al., (Molecular Biology of Homo Sapiens, Cold Spring Harbor Lab., 1986, pp. 285–297).

*Primary Examiner*—Margaret Moskowitz
*Assistant Examiner*—Ardin H. Marschel
*Attorney, Agent, or Firm*—Merchant, Gould, Smith, Edell, Welter & Schmidt

[57] ABSTRACT

Single base pair differences between otherwise identical DNA fragments can result in an altering of the melting behavior which can be detected by denaturing gradient gelelectrophoresis (DGGE). A method has been developed for efficient transfer of genomic DNA fragments from the gel following DGGE. The DGGE is run in a polyacrylamide gel (PAG) containing 2% low gelling temperature agarose (LGT). The PAG is crosslinked with a reversible crosslinker, and after electrophoresis the crosslinks are cleaved and 80–100% of the DNA fragments are transferred to nylon membranes by alkaline transfer. Hybridization with gene specific probes is then performed. The technique has been used to identify an RFLP in the COLIA2 gene.

9 Claims, 5 Drawing Sheets

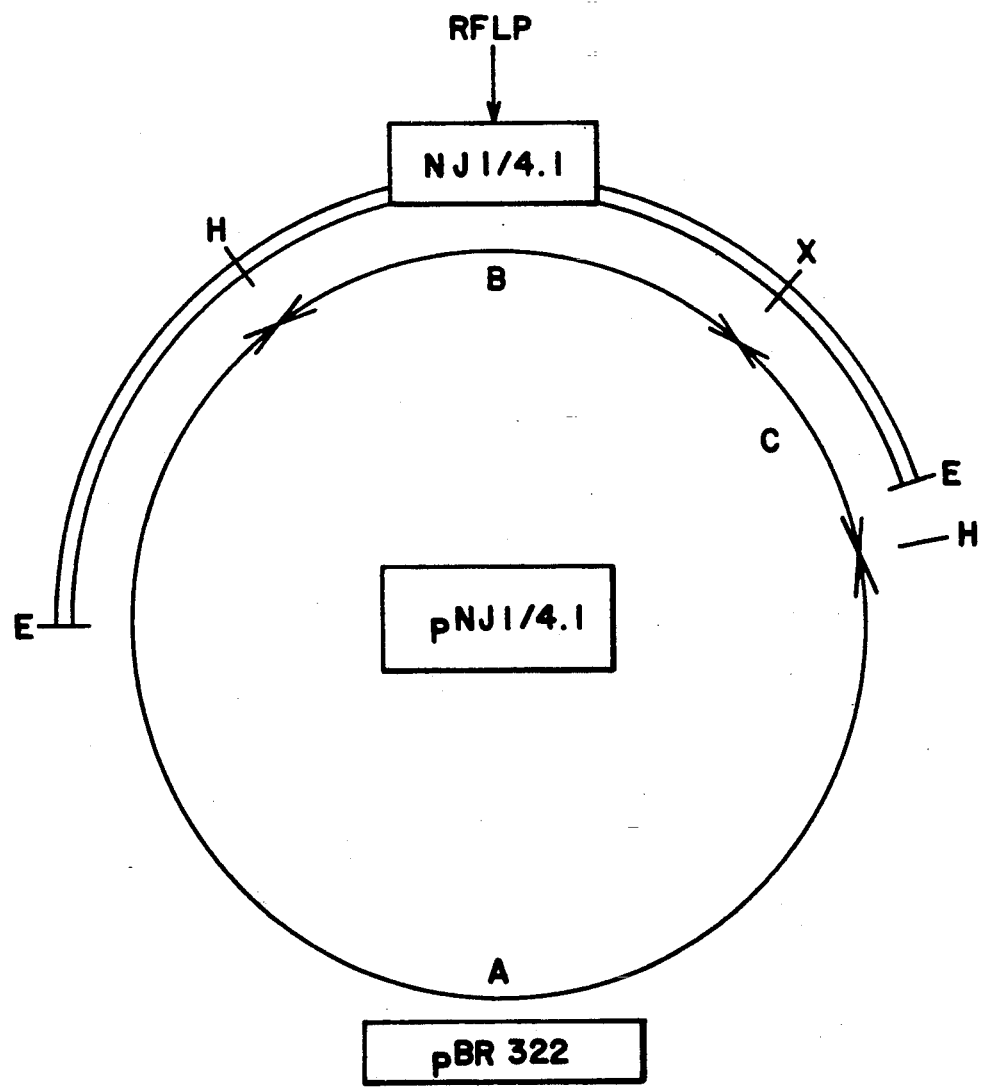

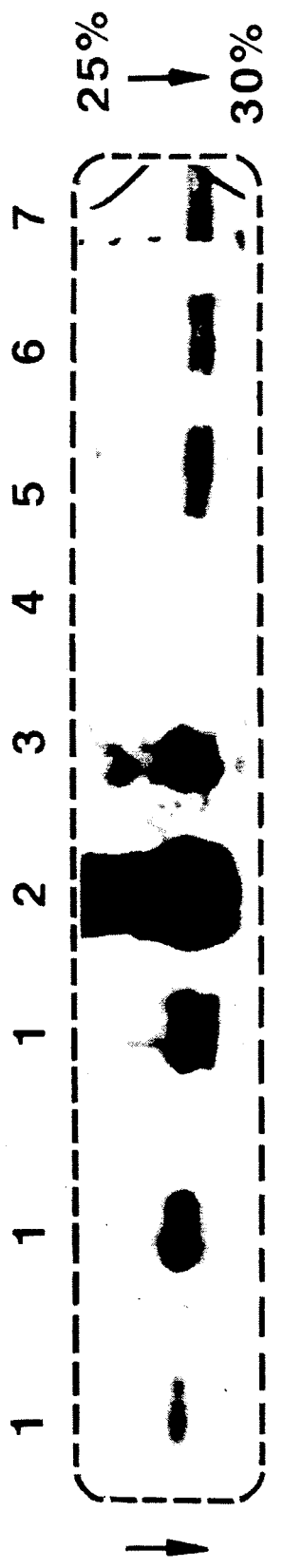

FIG. 4

Gel after blotting and transfer

Membrane after blotting and transfer

Membrane hybridized to probe MJ 1/4 labeled by random priming to a specific activity of $2 - 10^9$ cpm/µg 1. NJ 1/4 1 (H + X digest) endlabeled fragments
2. NJ 1/4 1 (H + X digest) 50 ng nonlabeled
3. NJ 1/4 1 (H + X digest) 5 ng nonlabeled
4. NJ 1/4 1 (H + X digest) 0.1 ng nonlabeled
5. Human genomic DNA (H + X digest) 40 µg
6. Human genomic DNA (H + X digest) 20 µg
7. Human genomic DNA (H + X digest) 10 µg

METHOD AND APPARATUS FOR DETECTING SINGLE BASE MUTATIONS IN DNA WITH DENATURING GRADIENT ELECTROPHORESIS

The invention relates to a method for the detection of single base mutations in multiple loci in human genomic DNA.

One aspect of the invention relates to a method of performing screening programs for genomic DNA for the detection of single base mutations.

Another aspect of the invention relates to a device for carrying out such screening programs.

The ability to detect single base mutations in human genomic DNA is of fundamental importance in the diagnosis of genetic diseases and in the detection of both induced and spontaneous mutations in malignant cell lines. Southern blotting technique to detect the absence or presence of restriction enzyme recognition sequences is limited by the fact that most single based substitutions do not alter a restriction endonuclease recognition sequence.

A recently developed method significantly increases the number of single base mutations that can be detected in a particular DNA fragment. The method is based on the melting behaviour of the DNA fragments and the use of denaturing gradient gelelectrophoresis as shown by Fischer, S. G. and Lerman, L. S. (1983) Proc. Natl. Acad. Sci. USA 80: 1579-83; Myers, R. M., Fischer, S. G., Maniatis, T. and Lerman, L. S. (1985) Nucl. Acids Res. 13: 3111-3129; Lerman, L. S., Silverstein, K. and Grinfeldt, E. in Molecular Biol. of *Homo Sapiens*, Cold Spring Harbor Lab. (1986) pp. 285-297. DNA fragments differing by single base substitutions can be separated from each other by electrophoresis in polyacrylamide gels containing an ascending gradient of the DNA denaturants urea and formamide. Two identical DNA fragments differing by only one single base pair, will initially move through the polyacrylamide gel at a constant rate. As they migrate into a critical concentration of denaturant, specific domains within the fragments melt to produce partially denatured DNA. Melting of a domain is accompanied by an abrupt decrease in mobility. The position in the denaturant gradient gel at which the decrease in mobility is observed corresponds to the melting temperature of that domain. Since a single base substitution within the melting domain results in a melting temperature difference, partial denaturation of the two DNA fragments will occur at different positions in the gel. DNA molecules can therefore be separated on the basis of very small differences in the melting temperature.

However, the previously described techniques to analyse genomic DNA fragments by the use of denaturing gradient gelelectrophoresis (DGGE) are based on two steps prior to electrophoresis: 1) denaturing of DNA fragments and 2) re-annealing of strands to a radioactive labelled probe (Myers, R. M. and Maniatis, T. (1986) in Molecular Biol. of *Homo sapiens*. Cold Spring Harbor Lab. pp. 275-284; Noll, W. W. and Collins, M. (1987) Proc. Natl. Acad. Sci. USA 84: 3339-3343). These techniques therefore limit the number of different loci to be analysed to one in each run and only minor sequence variations in a small DNA region can be detected. The probes that can be used are limited to genomic probes if not only exons are to be analysed. The object of the present invention is to develop a method for efficient transfer of partially melted genomic DNA fragments from the polyacrylamide gel, to be able to analyse for mutations in several different loci on the same DNA sample using a number of different probes on the same blot. The problems with the previously described transfer techniques have been that only a few percent of the fragments were transferred from these DG gels. The method of the invention should therefore greatly facilitate the identification of DNA polymorphisms not detected by restriction enzymes in a large number of different loci. This technique should therefore also be useful in screening for mutations within any DNA fragment where a probe exists.

The invention will now be illustrated with reference to the accompanying figures in which:

FIG. 2 is a schematic diagram of the plasmid NJ1/4.1,

Figure 1:
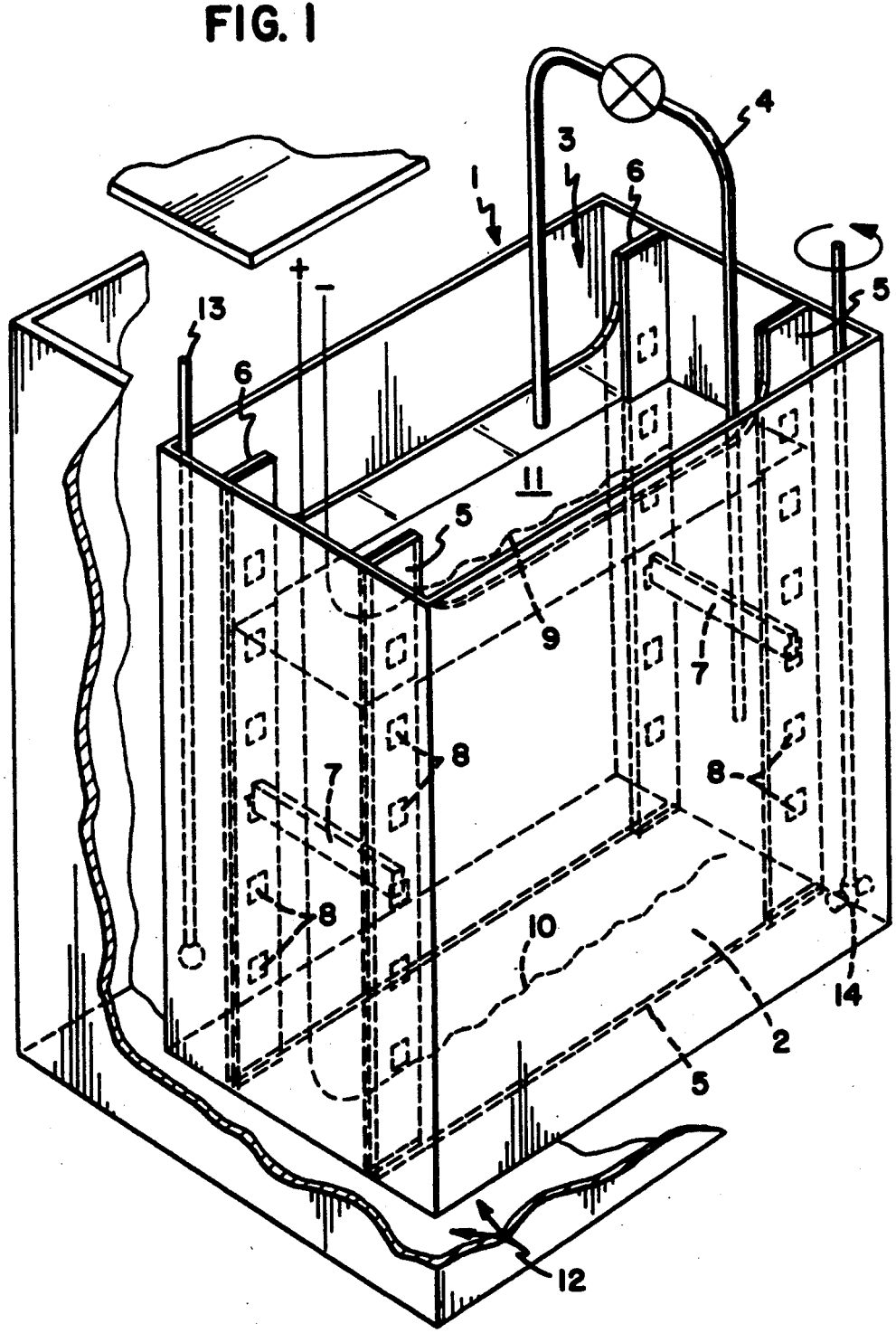
FIG. 1 shows an apparatus which may be used in the invention.

In particular the apparatus shown in FIG. 1 consists of a rectangular vessel 1 with a lower buffer compartment 2 and an upper buffer compartment 3 connected to each other via a pump circuit, two parallel glass plates 5, 6 for reception of the gel to be electrophoresed, arranged at a distance from each other by means of spacers 7 and clamps 8, and an upper 9 and lower 10 electrode for electrophoresis of the gel 11, all immersed in a water bath 12 equipped with a thermostat 13 and a stirrer 14 for direct control of the temperature in the rectangular inner vessel containing the glass plates.

FIG. 2 is a sketch of the model plasmid NJ1/4.1 containing a portion of a human collagen gene (COLIA2). The restriction site for the enzymes HindIII, XbaI and EcoRI is marked with H, X and E, respectively. The fragments A, B and C resulting from cleavage with the enzymes H+X are also marked.

Figure 3A:
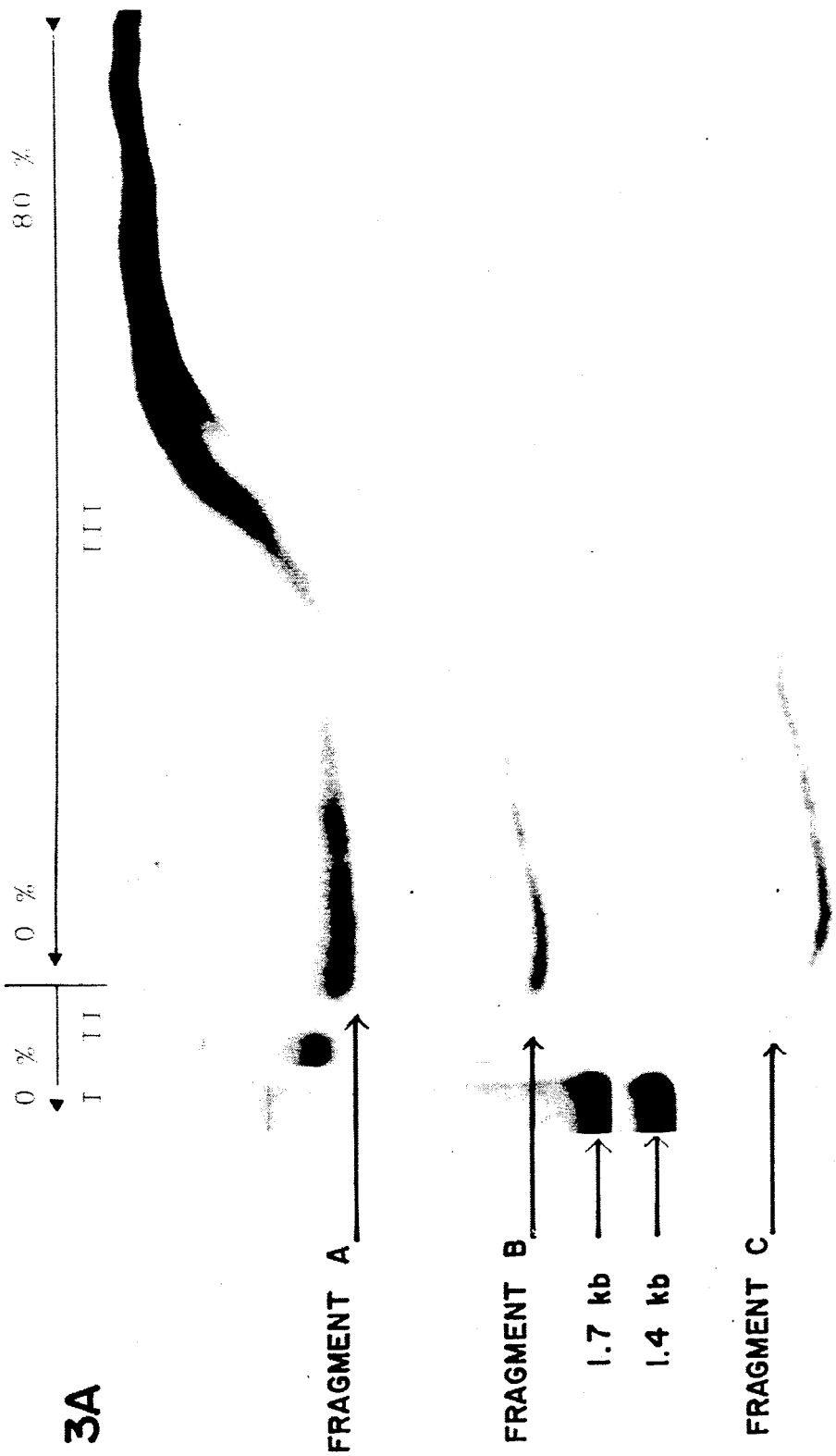
FIG. 3a is an autoradiogram of the gel itself where radioactive fragments from the plasmid NJ1/4.1 have been run in perpendicular DGGE.

FIG. 3a shows an autoradiogram of a DGGE gel. The plasmid NJ1/4.1 was first cleaved with the enzymes HindIII and XbaI, endlabelled with radioactive nucleotides, and then applied along the entire gel and run in a perpendicular gradient from 0 to 80% denaturant. In a 0-field, a standard with a cut of a plasmid giving known DNA fragment sizes was run.

Figure 3B:
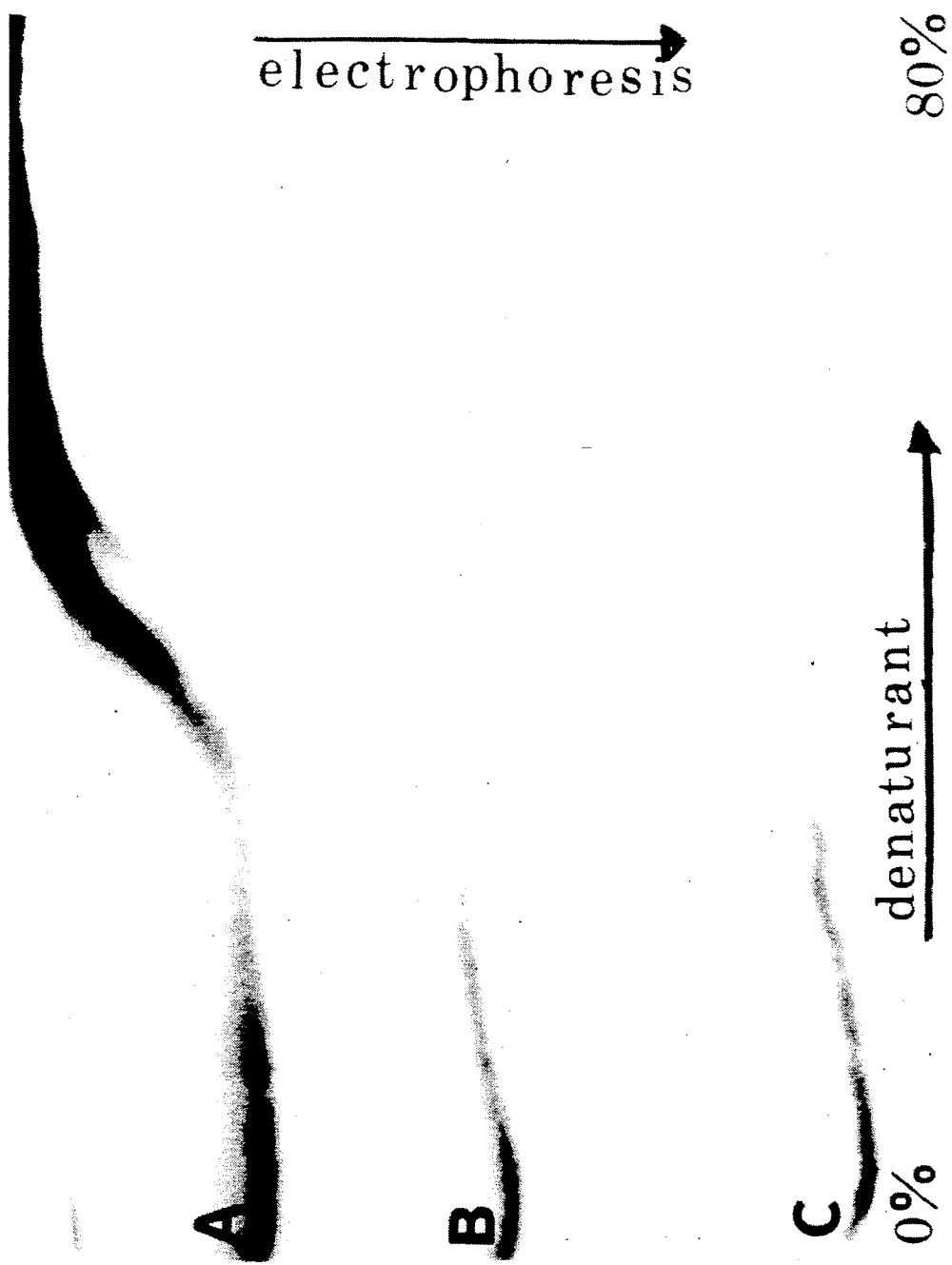
FIG. 3b is an autoradiogram of the membrane after transfer of fragments from the gel shown in FIG. 3a, and FIG. 4 is an autoradiogram of genomic DNA fragments hybridized with NJ1/4.1 after parallel DGGE and transfer to the membrane.

FIG. 3b shows an autoradiogram of the gel in FIG. 3a after transfer of the fragments to a membrane according to the invention.

FIG. 4 shows unlabelled fragments of NJ1/4.1 cleaved by enzymes H+X as well as genomic DNA cleaved with H+X which are run in parallel DGGE with a gradient of 25-30% denaturant. After the completion of electrophoresis, the fragments were transferred to a membrane as described below and hybridized with the probe NJ1/4.1 which had been made radioactive in advance using the methods described (random priming method).

EXAMPLE

The gels were prepared from 7,5% acrylamide and 2% low gelling temperature agarose (LGT) in TAE buffer (40 mM Tris pH 7, 4, 20 mM sodium acetate and 1 mM EDTA) with a linearly increasing concentration gradient of formamide and urea. 100% denaturant is equal to 40% formamide+7M urea. The acrylamide solution contained the reversible crosslinker diallyl tartardiamide (DATD) (Acrylamide: DATD=12, 5:1) instead of bisacrylamide. Solutions of acrylamide, agarose and denaturant were mixed to give two solutions for pouring a gradient with the desired denaturant concentration range. The gels were poured between two glass plates (20×20 cm) with a 1,5 mm spacer by mixing the two solutions of different denaturant concentrations in a linear gradient mixer and dripping by gravity into the top or side of the plates for parallel or perpendicular gels respectively. Immediately prior to pouring, ammonium persulfate (30 μl, 200 mg/ml) and TEMED (12 μl) were added to each solution. All the chemicals used to prepare the gels were highly purified electrophoretic grade.

Human genomic DNA was isolated from EDTA-anticoagulated whole blood by the Triton X-100 lysis method described by Kunkel et al. (1977), Proc. Natl. Acad. Sci. Isolated DNA samples were digested with the restriction enzyme HindIII at 37° C. overnight using 4 enzyme units/μg DNA followed by a second cleavage with the restriction enzyme XbaI. All the samples were analyzed by Southern blot using a probe for collagen (I)α-2 chain (COLIA2 gene) to determine the size of the fragments. DNA transfer was performed by alkaline blotting and hybridization was performed in 0.5M phosphate buffer with 7% SDS, pH 7,2 at 65° C. (Borresen, A. L. (1986). Annals of Clin. Res. 18: 258-263).

Plasmid preparation of plasmid NJ1/4.1 containing a 4.1 kb fragment of the human COLIA2 gene was performed using standard culturing methods (Maniatis, T., Fritsch, E. F. and Sambrook, J. (1982) Molecular Cloning: A Laboratory Manual, Cold Spring Harbor Laboratory, Cold Spring Harbor, N.Y.). The plasmid was cleaved with the restriction enzymes HindIII and XbaI giving three different fragments. These fragments were radioactively labelled by endlabelling using the large fragment (Klenow) of DNA polymerase I (Amersham) and 0,2 μm of each of dGTP, dATP, dTTP and (alfa-$^{32}$p)-dCTP (Amersham) at room temperature for 30 minutes according to the above method (Maniatis).

Radioactive labelling of the plasmid NJ1/4.1 for hybridization was performed by means of the random priming method using a commercially available kit from Amersham (Feinberg, A. P. and Vogelstein, B. (1983). Anal. Biochem. 132).

The electrophoresis was run in an aquarium of TAE buffer heated to 60° C. in an apparatus as shown in FIG. 1. In this apparatus two gels can be electrophoresed at a time. The gels were electrophoresed at 100-150 volts and 20-30 mA for 16-20 hours. After electrophoresis one of the glass plates was removed, and the gel transferred to the smooth side of a piece of benchcoat. When radioactively labelled fragments were electrophoresed, the gel was wrapped in Saranwrap and autoradiographed at −70° C. for 1-5 hours.

Before transfer of fragments from the gradient gels the crosslinks in the polyacrylamide gel were removed. The gel, resting on the smooth side of the benchcoat, was transferred with the benchcoat to a tray, and a solution of 2% periodic acid was carefully poured over the gel. After 30-40 minutes at room temperature the periodic acid solution was soaked off and a TS solution (0,4M NaOH+0,6M NaCl) was carefully poured into the tray to cover the gel. After 30 minutes the TS solution was soaked off and a filterpaper (Whatman 1), soaked in TS, was placed on top of the gel. The sandwich with the benchcoat, gel and filterpaper was then placed on top of a Southern transfer apparatus with the filterpaper side down. The benchcoat was removed and a nylon membrane, soaked in distilled water (Zeta probe, Biorad), was placed on top of the gel, and covered with several sheets of filterpaper and paper tissue. A weight of approximately one kilogram was placed on top. Blotting was performed in alkaline solution (TS) for 5-6 days. After blotting, the membrane was carefully removed from the gel, and if radioactively labelled fragments were to be analysed, both the gel and the membrane were wrapped in Saranwrap and autoradiographed separately. Membranes with non-radioactive DNA were neutralized and hybridized with $^{32}$P-labelled probes in 0,5M phosphate buffer, pH 7,2, with 7% SDS at 65° C. overnight, followed by high stringency washes in 1-0, 5% SDS at 65° C. Autoradiographs were developed at −70° C. using Amersham hyperfilm-MP.

RESULTS

The plasmid NJ1/4.1 contains a part of the COLIA2 gene and detects two RFLPs which has previously been described (Borresen, A. L. (1986). Annals of Clin. Res. 18: 258-263). Using the restriction enzymes HindIII and XbaI the plasmid is cut into three fragments, 5,2 kb, 2.1 kb, and 1.1 kb in size determined by Southern blot analysis. The 2.1 kb fragment (fragment B, FIG. 2) contains one of the RFLPs, namely the MspI polymorphism. The three fragments were endlabelled and used as a model system in the DGGE, the transfer and hybridization experiments. Perpendicular DGGE in the gradient from 0-80% of the three fragments showed that fragment B had a nice S-shaped melting curve with a melting point of approximately 32% denaturation (FIG. 3a). The prolonged alkaline transfer after removing the reversible crosslinking in the polyacrylamide gel by periodic acid showed that 80-100% is transferred to the nylon membrane (FIG. 3b). Unlabelled NJ1/4.1 HindIII+XbaI fragments were electrophoresed and transferred to nylon membranes using the same conditions as for the labelled fragment. Hybridization of the membrane with labelled probes (labelled by random priming) showed that hybridization did occur with all configurations of the fragments. Human genomic DNA digested with HindIII+XbaI gave three fragments (2.1 kb, 1.3 kb, 1.15 kb) hybridizing to the NJ1/4.1 probe on a Southern blot. The largest fragment corresponds to fragment B in the plasmid, and thus contains the MspI polymorphism with one single base mutation. Perpendicular DGGE of human genomic DNA fragments (150 μg of the HindIII+XbaI digest) showed that the two shortest fragments have melting curves different from fragment B, and would therefore not interfere in the interpretation of the results in the parallel gels.

Parallel denaturating gradient gels with plasmid fragments and human genomic DNA fragments showed hybridization down to approximately 10 pg plasmid or 10 μg genomic DNA. This gives a detection limit approximately that of a Southern analysis (FIG. 4).

DNA from both heterozygote and homozygote individuals for the MspI polymorphism was digested with HindIII+XbaI and run on parallel denaturating gradient gels followed by transfer, blotting and hybridization to the NJ1/4.1 probe. Different migration of band B in the different individuals was observed. Thus a single base difference in fragment B between individuals could be detected in analysis of genomic DNA by this technique.

The denaturating gradient gel electrophoresis technique described by Fisher and Lerman is capable of detecting over 50% of all possible single base substitutions in DNA fragments of 100–1000 bp in length. If the probes are linked to a GC-rich small DNA fragment, it seems that more than 90% of all possible base substitutions can be detected. A limitation of this previously described technique, however, is that it involves the use of single stranded probes, and solution hybridization before electrophoresis. Therefore the DNA in the gel cannot be used with other probes and only sequence variation in a small DNA region can be detected after an electrophoresis. Total genomic DNA cut with restriction enzymes into small fragments can be submitted to denaturating gradient gel electrophoresis directly. However, there have been great difficulties in transferring these fragments with different entanglements from the polyacrylamide matrix to a membrane. Electroblotting transfers only approximately 10% of the DNA, and will also cause swelling of the gel making it difficult to compare the band pattern from each individual. The technique described here, however, using a polyacrylamide agarose mix and a reversible crosslinker in the PAG solves the transfer problem. After removal of the crosslink, the gels can easily be equilibrated with TS and no swelling occurs. The low gelling temperature agarose makes it possible to pour the gels at 25° C., and the gradient can be formed slowly, which is very important. Since the gels are run at 60° C., low gelling temperature agarose rather than low melting temperature agarose has to be used. The agarose gel after removal of the polyacrylamide crosslinking is not very strong, so the gels have to be handled with care, but by using benchcoat it is easy to handle this sandwich. Blotting in TS was most efficient after 4–6 days.

The modification of the DGGE with the transfer technique described here would greatly facilitate the analysis of DNA variation in genomic DNA where restriction enzymes do not pick up a difference. To examine genomic DNA for mutation or variation in several different loci, the following strategy should be performed: First determine the restriction enzymes which give a suitable number of small fragments (300–2000 kb) on Southern blot analysis. Then run a perpendicular gradient gel to determine the melting curve of the different fragments. This perpendicular gradient gel on one particular restriction cut of DNA can be used for several different probes after blotting. Then three parallel gradient gels are run with gradients from 0–30, 30–60 and 60–90% denaturation respectively. For one particular probe the denaturation gradient that includes the melting point of the fragment of interest is used.

With this strategy a screening for single base mutation within a number of different loci to detect mutations in malignant cell lines, or DNA variation in different individuals, can be performed on a single DNA sample. Automation of this technique will probably bring down the cost of these experiments and give even more widespread application of this technique.

The technique may be used in screening programs for genetic diseases, for genes that predispose for diseases like coronary heart disease (CHD) and cancer, in monitoring individuals for increased mutation and in test systems for evaluating a drug for its mutagenic activity.

I claim:

1. A method for detection and screening of genomic DNA for single base mutations in multiple loci, said method comprising subjecting genomic DNA fragments, said genomic DNA having sufficient size to include multiple loci that can each exhibit single base pair mutations, to denaturing gradient gel electrophoresis (DGGE) in a reversibly crosslinked gel medium, said medium comprising a polyacrylamide, a low gelling temperature agarose and a denaturant in a gradient perpendicular to the direction of electrophoresis followed by a transfer to a support membrane and hybridization to various selected probes.

2. The method according to claim 1 wherein all restriction fragments of genomic DNA are used and the differences in the physical melting points, which occur for otherwise identical DNA fragments result from a mutation of a single base pair.

3. The method according to claim 2 wherein the denaturant is formamide and urea having a linearly increasing concentration gradient, where 100% denaturing corresponds to 40% formamide+7M urea.

4. The method according to claim 2 wherein the gel for the electrophoresis contains 5–15% of a polyacrylamide gel and 1–2% low gelling temperature agarose and buffer.

5. The method according to claim 4 wherein the crosslinking agent is diallyl tartardiamide and the ratio between diallyl tartardiamide and acrylamide is from 1:10 to 1:30.

6. The method according to claim 4 wherein the crosslinking agent is diallyl tartardiamide and the ratio between diallyl tartardiamide and acrylamide is about 1:12.5.

7. The method according to claim 5 wherein after electrophoresis the gel is treated with aqueous periodic acid to cleave the reversible crosslinking in the gel.

8. The method according to claim 7, wherein the DNA fragments from the gel with the cleaved crosslinking agent are transferred to a nylon membrane by alkaline transfer and that hybridization with gene specific probes is carried out.

9. A method according to claim 1 wherein the gel medium includes at least two different types of gel and the electrophoresis is conducted at a current of 20–30 mA, a voltage of 100–150 volts, and within a temperature range of 50°–60° C. for a period of 16–20 hours.

* * * * *